United States Patent [19]
Braun

[11] Patent Number: 5,898,530
[45] Date of Patent: Apr. 27, 1999

[54] RADIATION APPARATUS

[75] Inventor: Werner Braun, Wilen, Switzerland

[73] Assignee: Maxs AG, Sachseln, Germany

[21] Appl. No.: 08/423,819

[22] Filed: Apr. 19, 1995

[30]  Foreign Application Priority Data

Apr. 21, 1994 [DE] Germany .......................... 94 06 682 U

[51] Int. Cl.⁶ ............... G02B 5/24; G02B 5/22; F21V 9/04; F21V 5/00
[52] U.S. Cl. ................ 359/886; 359/892; 359/350; 359/358; 362/318; 250/504 R
[58] Field of Search ..................... 359/350, 358, 359/886, 892; 250/504 R, 504 H, 505.1; 362/318

[56]  References Cited

U.S. PATENT DOCUMENTS

| | | | |
|---|---|---|---|
| 2,380,682 | 4/1945 | Boerstler | 359/358 |
| 2,783,682 | 3/1957 | Swenson . | |
| 3,572,907 | 3/1971 | Cindrich . | |
| 3,914,010 | 10/1975 | Zeller | 359/358 |
| 4,789,784 | 12/1988 | Grossman et al. | 359/358 |
| 4,939,374 | 7/1990 | Greutert | 359/892 |

FOREIGN PATENT DOCUMENTS

| | | |
|---|---|---|
| 0311898 B1 | 3/1990 | European Pat. Off. . |
| 40 42 259 | 6/1992 | Germany . |

Primary Examiner—Jon W. Henry
Assistant Examiner—Audrey Chang
Attorney, Agent, or Firm—Tilton, Fallon, Lungmus & Chestnut

[57]  ABSTRACT

A radiation apparatus comprising a radiation source and a filter arranged in an optical path, said filter comprising two transparent filter discs which are arranged substantially in plane-parallel fashion relative to each other and which are held with their surrounding edges in a frame made of a material of good heat conduction, the filter discs and the frame defining a closed cavity which has provided therein a medium for selectively influencing the radiation spectrum. The frame is divided substantially in a direction transverse to the filter axis into first and second frame halves in such a manner that the one filter disc is arranged on the first frame half at the side facing the cavity and the other filter disc is arranged on the second frame half at the side facing the cavity.

14 Claims, 5 Drawing Sheets

RADIATION APPARATUS

BACKGROUND OF THE INVENTION

1. Field of the Invention

The present invention relates to a radiation apparatus comprising a radiation source and a filter which is disposed in an optical path and comprises two transparent discs which are arranged substantially in plane-parallel fashion to each other and which are held with their surrounding edges in a frame made of a material of good heat conduction, the discs and the frame defining a closed cavity which has provided therein a medium for selectively influencing the radiation spectrum.

2. Description of the Related Art

Such a radiation apparatus is, for instance, known from EP-A-0311898. The radiation apparatus described in the publication is used for heat therapy, especially of the human body. The purpose of the filter used in this apparatus is that the radiation spectrum in its entirety as emitted by the radiation source is suited for heat therapy to a limited degree. That is why specific bands of the radiation spectrum are filtered out by the filter. The known filter consists of a multipart frame which is composed of an outer frame connected to the housing of the radiation apparatus and of an alternate frame which is arranged therein and carries both filter discs. Two press rings are arranged on the alternate frame for pressing the two filter discs each in tho direction of the cavity onto their seals. At least one of the press rings is undetachably connected to the alternate frame by way of a flanging operation.

It is the object of the present invention to improve a radiation apparatus of the above-mentioned type in such a manner that the structure of the filter becomes more simple.

SUMMARY OF THE INVENTION

This object is attained according to the invention in that the frame is divided substantially in a direction transverse to the filter axis into first and second frame halves, that the one disc is arranged on the first frame half at the side facing the cavity and that the other disc is arranged on the second frame half at the side facing the cavity. The frame halves themselves now provide for an exact and stable arrangement of the filter discs owing to this bipartite structure without additional press rings being required. Furthermore the two frame halves can be arranged next to each other by means of detachable connecting means, so that even after some time of operation access will be guaranteed to the medium inside the cavity and also to the filter discs.

At least one of the discs is preferably inserted substantially with a snug fit in a surrounding step of the first and second frame halves. The step provides for a stop shoulder for the disc, so that the latter cannot be pressed out of its mounting by the pressure prevailing in the cavity.

The sealing effect of the filter can specifically be increased in that the edges of the discs rest each on a substantially surrounding seal at the side facing away from the cavity. In contrast to the prior art, the pressure inside the cavity ensures in this arrangement that upon increase in pressure the sealing effect is also increased, as the discs are pressed more and more strongly onto their seals.

Since the filter is arranged in the optical path of the radiation source, it is also exposed to extremely high temperatures. To improve convection of the medium inside the cavity, a surrounding annular chamber which communicates with the cavity may be arranged at least in one of the frame halves, whereby heat can be transported away more rapidly via the frame housing due to the increased contact surface between medium and frame. It is here of particular advantage that an annular chamber half is arranged in each of the two frame halves for forming a common and large annular chamber. A relatively large annular chamber in which an excellent heat exchange between frame and medium can take place is obtained by joining the two frame halves.

To seal the annular chamber to the outside in an improved manner, at least one surrounding seal may be arranged outside of the annular chamber in a frame half which rests on the other frame half.

It is of great importance to a correct functioning of the filter that the two discs are arranged substantially in plane-parallel fashion relative to each other and that they are also not moved out of their plane-parallel configuration by the thermal expansion of the medium and the resultant increase in pressure. To this end, a pressure compensating device may be provided in or on one of the annular chambers for compensating for pressure variations caused by the heating of the medium inside the cavity, and for receiving a possible accumulation of gas bubbles. Hence, the pressure compensating device ensures that the discs cannot be deformed by the internal pressure in the cavity.

It has been found to be of great advantage that the pressure compensating device consists of a compensating container which is in communication with an annular chamber and comprises a compensating chamber which is defined by a flexible membrane at least at one side. Upon rise or drop in pressure the flexible membrane will give way in a corresponding direction. In another variant of the pressure compensating device, a spring-loaded piston may be arranged in the compensating chamber of the compensating container for compensatingly moving in and out in case of pressure variations in the cavity.

Since the temperature of the filter disc facing away from the radiation source is substantially defined by the medium inside the cavity, the disc can also consist of a plastic material, preferably polycarbonate. The costs of the material can thus be reduced considerably.

The disc which faces the radiation source may preferably consist of a heat-resistant material, preferably mineral glass. When the radiation source is not quite so powerful, polysulfone can also be used; otherwise, a glass-ceramic material which is available on the market under the name "Robax" is preferred.

The heat received by the frame can be transmitted to the outside even more rapidly when cooling ribs are arranged on the outer circumference thereof.

The two frame halves can easily be fastened to each other in that some cooling ribs have a thickened structure and comprises through-holes aligned with respect to the first and second frame halves for receiving fastening means.

An embodiment of the invention shall now be explained in more detail with reference to a drawing, in which:

DETAILED DESCRIPTION OF THE PREFERRED EMBODIMENTS

Figure 1:
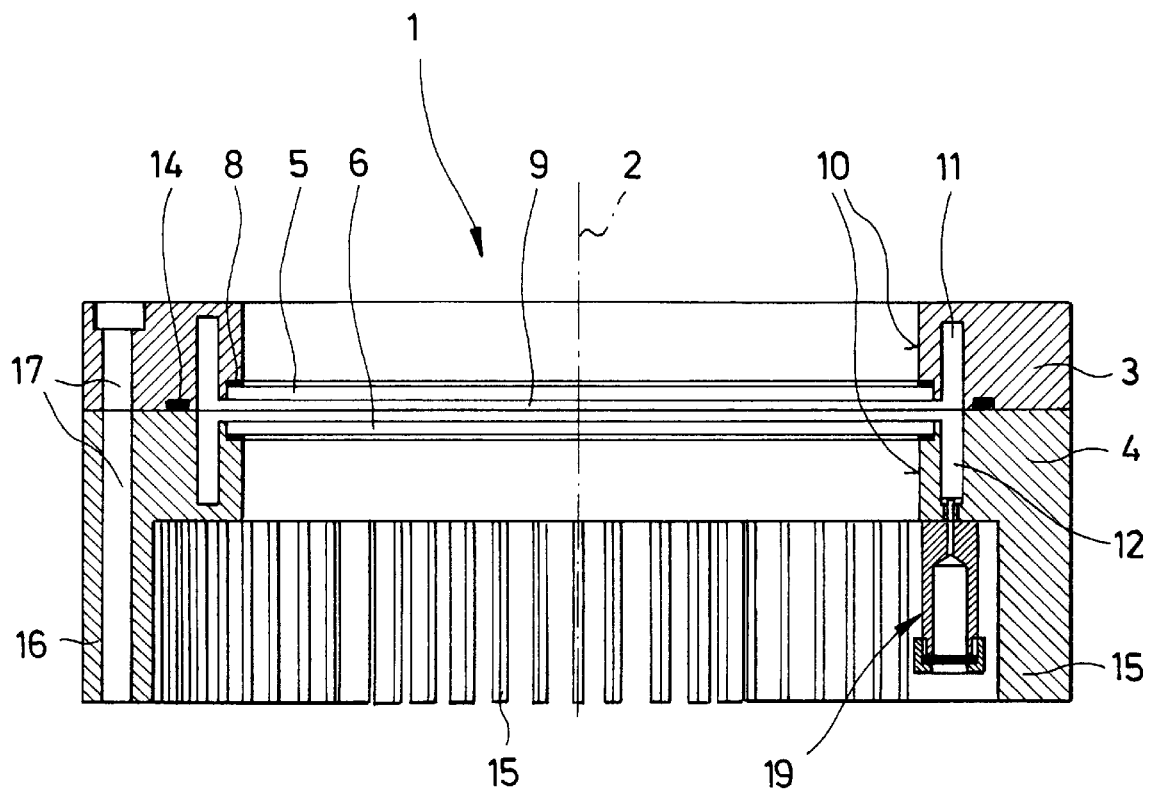
FIG. 1 is a full sectional view of a filter for use in a radiation apparatus of the invention.
Figure 2:
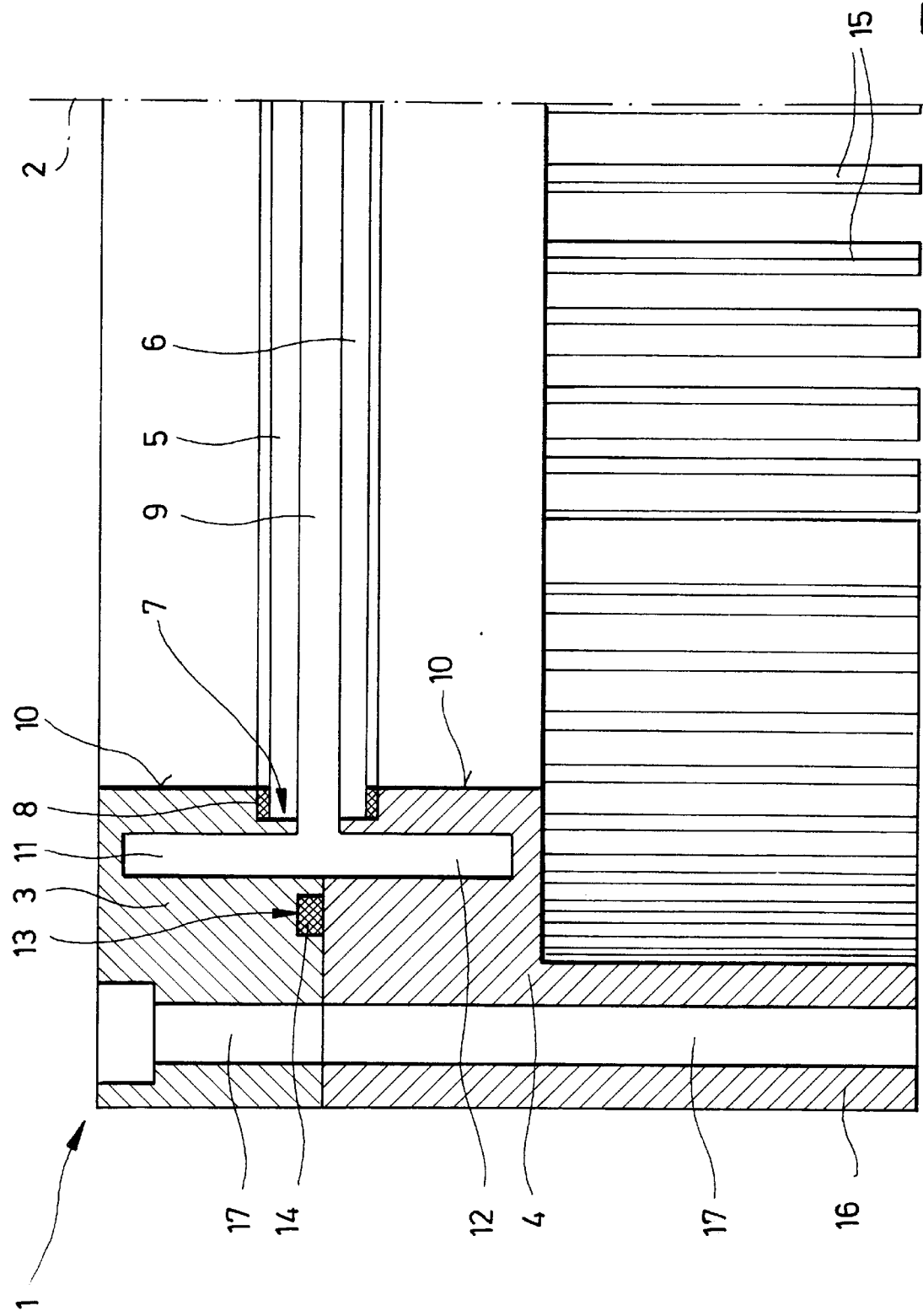
FIG. 2 is an enlarged section of the filter of FIG. 1.
Figure 3:
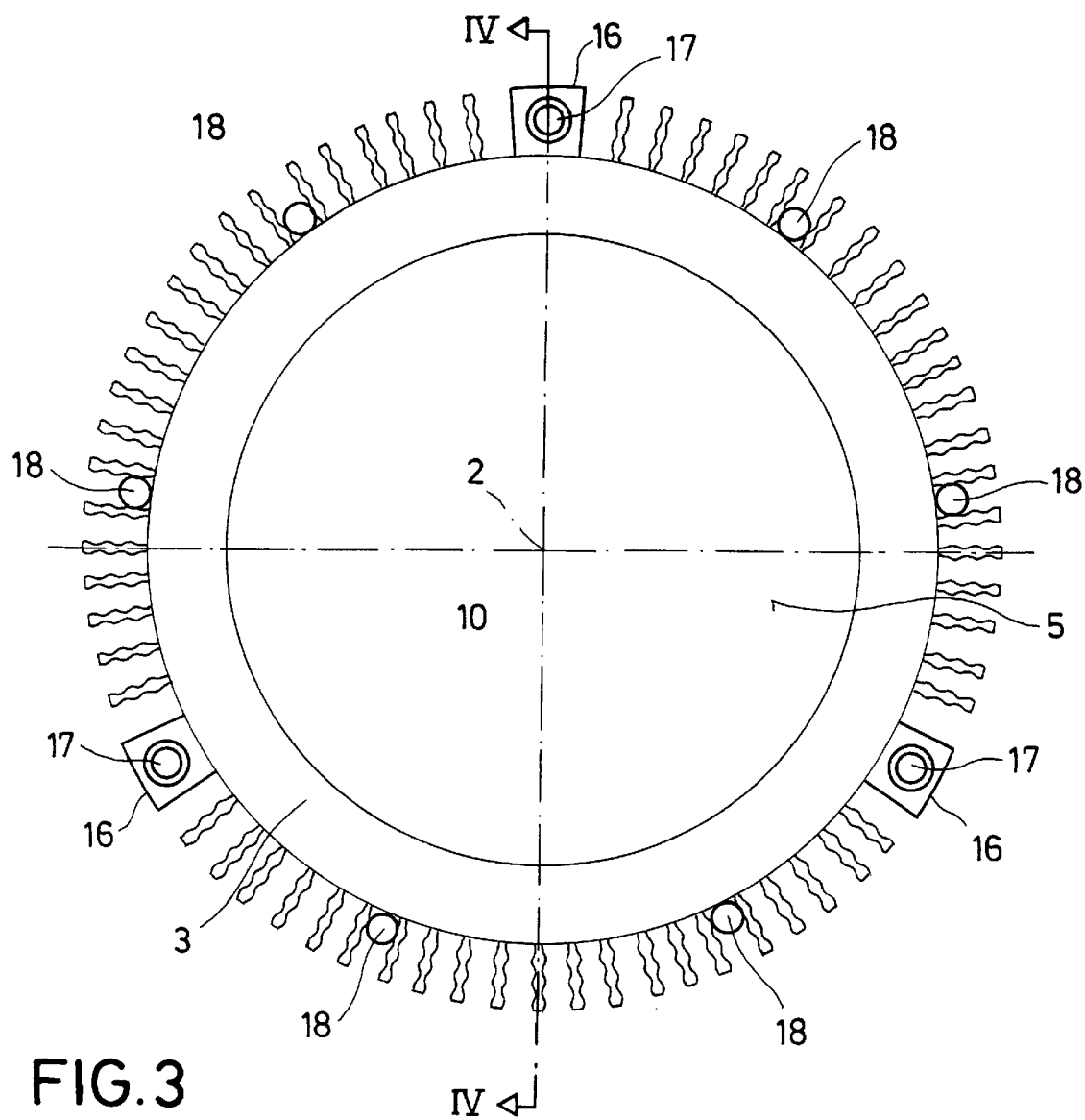
FIG. 3 is a top view of a first frame half with disc of the filter of FIG. 1.
Figure 4:
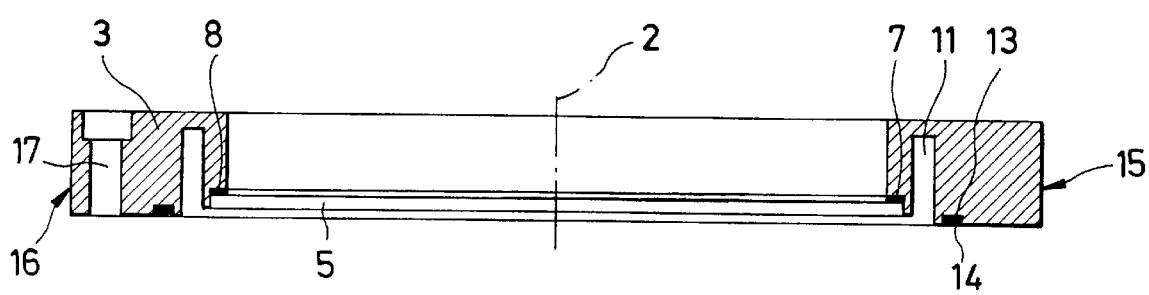
FIG. 4 is a sectional view of the first frame taken along line IV—IV in FIG. 3.
Figure 5:
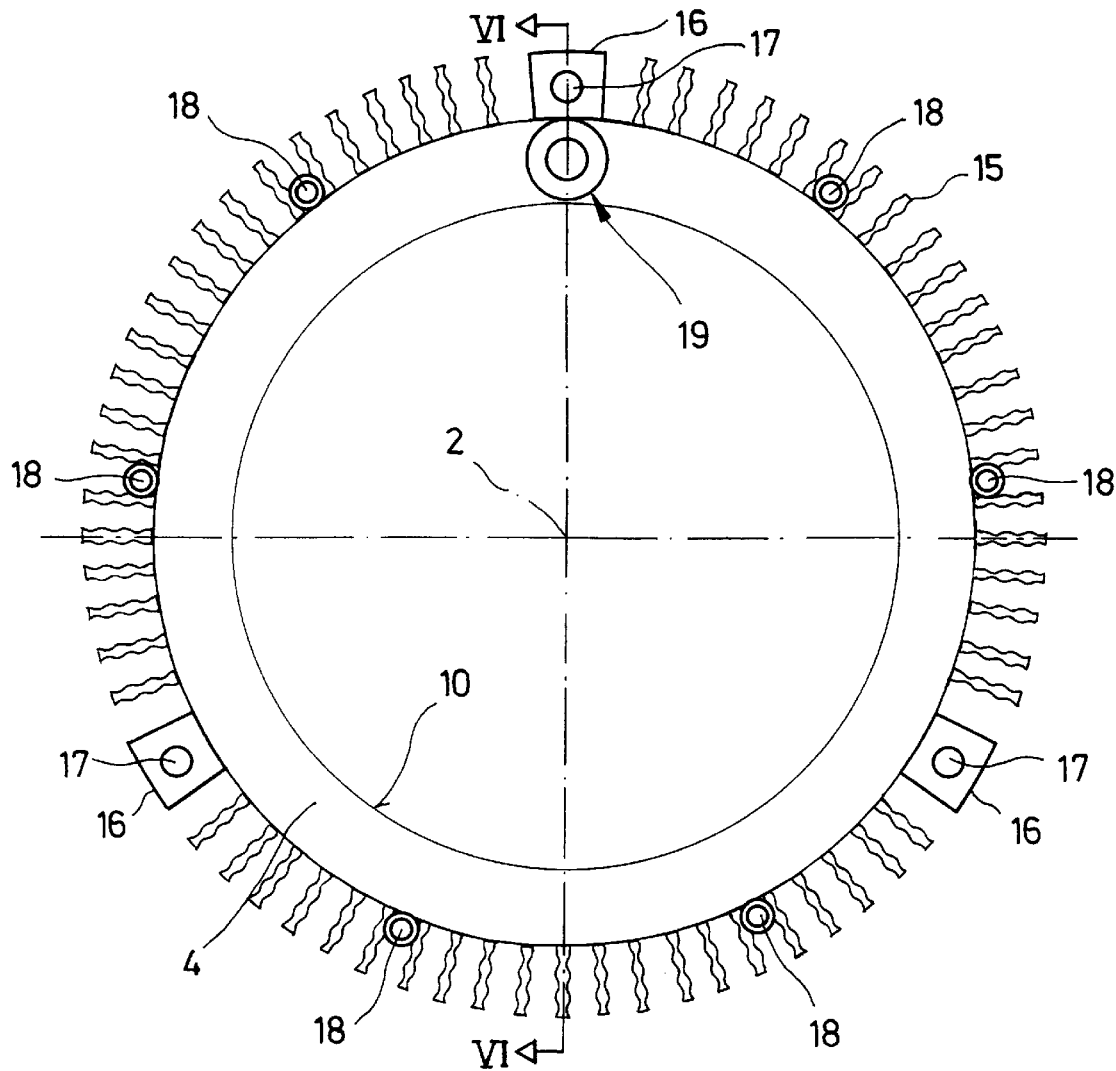
FIG. 5 is a top view of a second frame half of the filter of FIG. 1.

FIGS. 1 and 2 show a filter 1 which can be arranged in the optical path of a radiation source (not shown) of a radiation apparatus.

Filter 1 essentially consists of a frame which as a bipartite structure in a direction transverse to the filter axis and which consists of a first frame half 3 and a second frame half 5 and of a filter disc 4 facing away from the radiation source, and of a second filter disc 6 arranged in plane-parallel fashion thereto. To this end, the plane filter discs 5, 6 are inserted with a snug fit in a surrounding step 7 of the first and second frame halves 3, 4. On their edges filter discs 5, 6 rest each on a surrounding seal 8 at the side facing the bottom of step 7. Seal 8 can, for instance, consist of a suitable adhesive layer of silicone, so that filter discs 5, 6 are simultaneously secured by seal 8 in the corresponding frame halves 3, 4. Step 7 is respectively arranged in frame halves 3, 4 such that the two filter discs 5, 6 are arranged at a specific axial distance relative to each other and thus form a disc-shaped cavity 9 interposed thereinbetween. Said cavity 9 is filled with a medium selectively influencing the radiation spectrum to filter out specific bands of the radiation emitted from the radiation source. In filters for use in heat therapy the medium normally consists of water which has fungicides possibly added thereto.

To ensure passage of the radiation through the two filter discs 5, 6, the two frame halves 3, 4 are each provided with a relatively large through-hole 10 which is concentric to the filter axis 2.

The two frame halves 3, 4, have arranged therein annular chamber halves 11 and 12 which are concentric to the filter axis 2 and which communicate with cavity 9. To this end, cavity 9 is just left open along its outer edge relative to the annular chamber halves 11, 12. The annular chamber halves 11, 12 extend each in parallel with the filter axis 2 to the greatest possible extent into the respective frame halves 4, 4. The annular chamber halves 11, 12 are preferably introduced into the frame halves 3, 4 in the form of annular recesses. The annular chamber halves 11, 12 are also filled with the medium.

Since the annular chamber halves 11, 12 are also sealed to the outside, the first frame half 3 has a surrounding annular groove 13 which is arranged relative to the filter axis 2 outside of the annular chamber halves 11, 12 and has inserted therein a sealing ring 14 which in the plane of division of the first and second frame halves 3, 4 comes into sealing engagement with the second frame half 4.

As becomes apparent from the illustrations of the individual frame halves 3, 4 (see FIGS. 3–6), radially outwardly projecting cooling ribs 15 which may have a slightly waved shape for enlarging the surface and thus the cooling effect are arranged on the circumference of the first and second frame halves 3, 4. The cooling ribs 15 of the second frame half 4 are made substantially longer than the cooling ribs 15 of the first frame half 3 and are no longer connected to the main body of the second frame half 4 over a major portion of their length.

Instead of the relatively thin cooling ribs, enlarged webs 16 are arranged at regular intervals on the outer circumference of the frame halves 3, 4 in the same longitudinal extension as the cooling ribs 15. Webs 16 serve to accommodate longitudinal holes 17 into which fastening means (not shown) can be inserted for fastening to the housing (not shown) of the radiation apparatus. Furthermore, material accumulations 18 which have threaded holes in alignment on the first and second frame halves 3, 4 and into which fastening means (also not shown) such as screws can be inserted for connecting the two frame halves 3, 4 are molded between some cooling ribs at regular intervals.

The first filter disc 5 is not so strongly heated by the medium positioned in cavity 9, so that a less heat-resistant material can be used. The first filter disc 5 therefore consists of a plastic material, preferably polycarbonate. By contrast, the second filter disc 6 is directly exposed to the radiation source and is therefore heated considerably; that is why this disc preferably consists of a heat-resistant material, preferably mineral glass.

Figure 6:
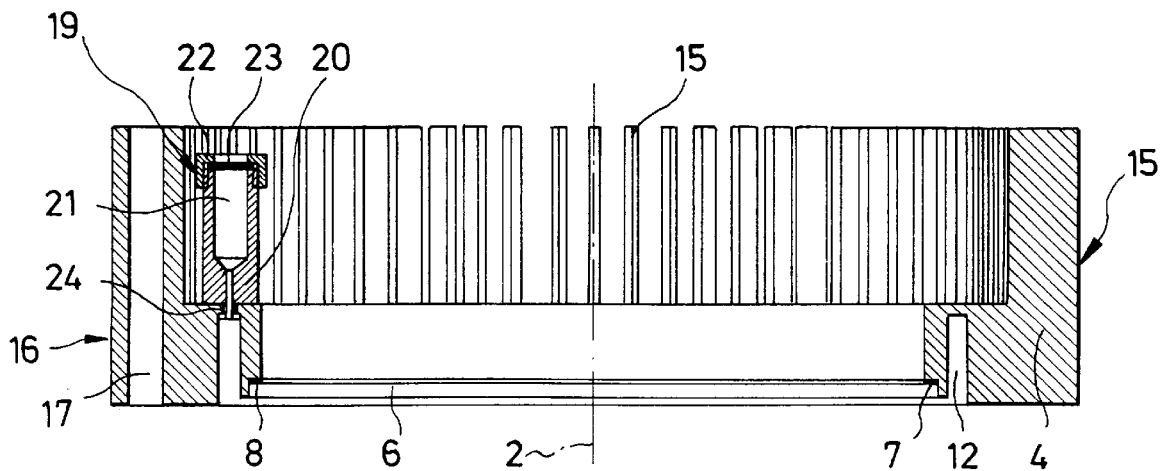
FIG. 6 shows the second frame half taken along line VI—VI in FIG. 5.
Figure 7:
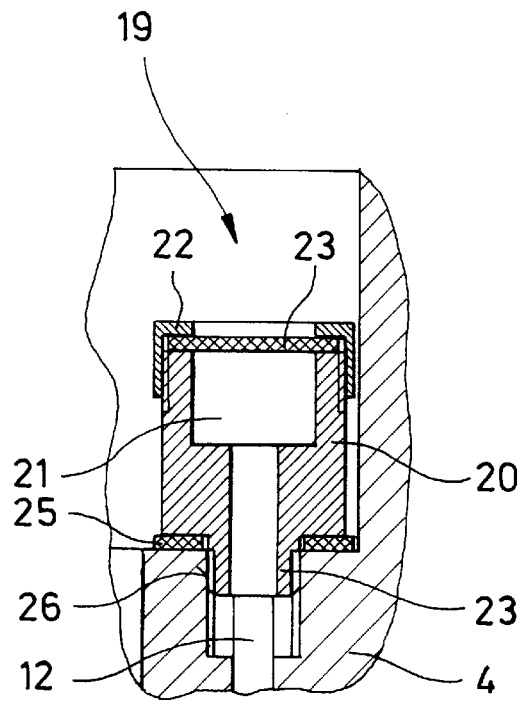
FIG. 7 is an enlarged sectional view of a second variant of a pressure compensating device.

As can especially be seen in FIG. 6, the second frame half 5 comprises a pressure compensating device 19 in communication with the annular chamber half 12, the pressure compensating device 19 compensating for pressure variations caused by the thermal expansion of the medium in cavity 9, and receiving a possible accumulation of gas bubbles. The illustrated pressure compensating device 19 consists of a compensating container 20 which is mounted on the second frame half 4 and has compensating chamber 21 which is closed by a screw cap 22. Screw cap 22 has an inspection window below which a flexible membrane 23 is arranged. A cylindrical hollow pin 24 which is pressed into a hole of the second frame half 4 or, as shown in FIG. 7, screwed thereinto and which extends up into the annular chamber half 12 for establishing a connection between annular chamber 12 and compensating chamber 21 is positioned at the lower end of the compensating container 20. It is here important to note that the connection point between pressure compensating device 19 and second frame half 4 is also tight. To this end, the variant of a pressure compensating device according to FIG. 7 has a seal 25 disposed between the compensating container 20 and the second frame half 4, which surrounds the hollow pin 23 provided with an external thread 26.

Figure 8:
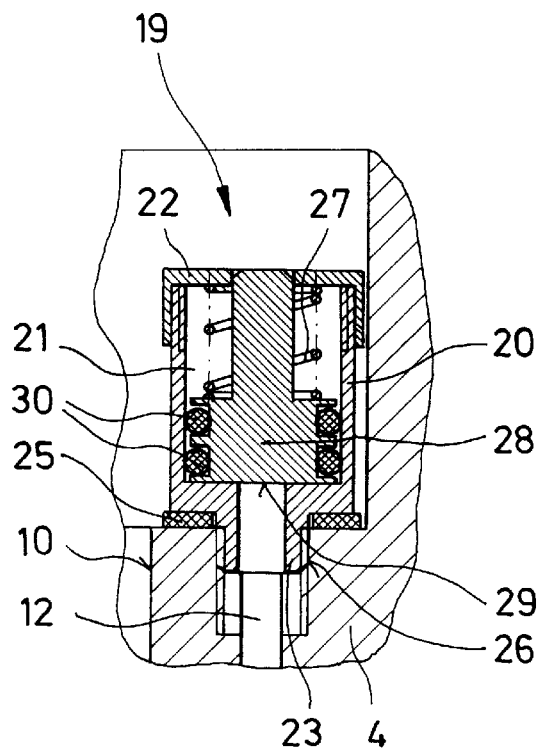
FIG. 8 is an enlarged sectional view of a third variant of a pressure compensating device.

FIG. 8 illustrates a further variant of a pressure compensating device in which a piston 28 loaded at one side by a pressure spring 27 is arranged in the compensating chamber 21 of the compensating container 20. To ensure that the medium is positioned only within the region of the compensating chamber 21 which is defined at one side by the front side 29 of piston 28, piston 28 is provided on its circumference with sealing rings 30 which are in contact with the compensating chamber wall.

To ensure an improved heat exchange, frame halves 3, 4 are each made of a material of high heat conduction, such as aluminum.

The mode of operation of the present invention shall now be explained in more detail.

First of all, the radiation source of the radiation apparatus is switched on, so that the source will emit rays in the direction of filter 1. These rays will first impinge on the heat resistant second filter disc 6 and then on the medium positioned within cavity 9, and then on the first filter disc 5. Since the second filter disc 6 is heated, the medium cavity 9 is also heated. Since the annular chamber halves 11,12 are in communication with cavity 9 and guarantee a good heat transmission from the medium to the frame halves 3, 4 owing to their relatively large surfaces, one obtains a natural convection within the medium. The heat exchange is chosen such that the medium will not reach its boiling point. For this reason, and on account of the fact that water is preferably used as the medium, the first filter disc 5 is heated to a relatively small degree in comparison with the second filter disc.

Apart from the possibility according to the present invention, i.e., to arranged the annular chamber halves 11, 12 in the above-described manner to provide for an enlarged surface, the present invention has the advantage that the filter discs 5 and 6 are pressed onto their respective seals 8 on account of the increase in pressure due to the heating of the medium in cavity 9. This takes place for the reason that the first filter disc 5 is arranged on the first frame half 3 at the side facing cavity 9 and the second filter disc 6 is arranged on the second frame half 4 at the side facing cavity 9. Hence, an increase in pressure in cavity 9 will automatically lead to an improved sealing. The pressure, however, must not exceed a specific value at which the filter discs 5, 6 would be deformed in an inadmissible manner and a lens effect would take place. A pressure compensating device 19 is therefore provided in combination with an annular chamber half 12, the flexible membrane 23 of the pressure compensating device 19 rather giving way in case of an increase in pressure, instead of filter discs 5, 6 deforming in an inadmissible manner. Furthermore, the pressure compensating device 19 serves to receive possible gas bubbles which have penetrated into the chamber, for instance, due to diffusion of gas along the outer seal.

In the variant of a pressure compensating device as shown in FIG. 8, the medium which expands upon heating presses against piston 28, the resilient force of pressure spring 27 being chosen such that filter discs 5, 6 do not deform inadmissibly due to an increase in pressure in cavity 9. It is however also possible to insert or screw a simple sealed plug into the reception hole provided therefor instead of a pressure compensating device.

I claim:

1. A radiation apparatus comprising a radiation source and a filter (1) which is arranged in an optical path and has two transparent filter discs (5, 6) which are substantially arranged in plane-parallel configuration relative to each other and which are held with their surrounding edges in a frame made of a material of good heat conduction, said filter discs (5, 6) and said frame defining a closed cavity (9) which has provided therein a medium for selectively influencing the radiation spectrum, wherein said frame is divided, substantially in a direction transverse to filter axis (2), into first and second frame halves (3, 4) in such a manner that said one filter disc (5) is arranged on said first frame half (3) at the side facing said cavity (9) and said other filter disc (6) is arranged on said second frame half (4) at the side facing said cavity (9), wherein on their edges said filter discs (5, 6) rest each on a substantially surrounding seal (8) at the side facing away from said cavity (9).

2. The radiation apparatus according to claim 1, wherein at least one of said filter discs (5, 6) is inserted substantially with a snug fit in a surrounding step (7) of said first and/or second frame halves (3, 4).

3. The radiation apparatus according to claim 1 or 2, wherein a surrounding annular chamber (11, 12) which communicates with said cavity (9) is arranged at least in one of said frame halves (3, 4).

4. The radiation apparatus according to claim 3, wherein said two frame halves (3, 4) have each arranged therein an annular chamber half (11, 12) for forming a common and large annular chamber.

5. The radiation apparatus according to claim 3, wherein said annular chamber has provided therein or thereon a pressure compensating device (19) which compensates for pressure variations caused by the heating of the medium within said cavity (9), and receives a possible accumulation of gas bubbles.

6. The radiation apparatus according to claim 5, wherein said pressure compensating device (19) consists of a compensating container (20) which is in communication with said annular chamber and comprises a compensating chamber (21) which is defined at least at one side by a flexible membrane (23).

7. The radiation apparatus according to claim 5, wherein said pressure compensating device (19) consists of a compensating container (20) which is in communication with said annular chamber and comprises a compensating chamber (21) having arranged therein a spring-loaded piston which resiliently moves in upon increase in pressure in said cavity (9).

8. The radiation apparatus according to claim 3, wherein at least one surrounding seal (14) is arranged outside of said annular chamber in one of said frame halves (3, 4), and said seal resting on the other said frame half (3, 4).

9. The radiation apparatus according to claim 1 or 2, wherein the filter disc (5) of said filter (1) which faces away from said radiation source consists of a plastic material.

10. The radiation apparatus of claim 9, wherein the plastic material is polycarbonate.

11. The radiation apparatus according to claim 1 or 2, wherein said filter disc (6) which faces said radiation source consists of a heat-resistant material.

12. The radiation apparatus of claim 11, wherein the filter disc (6) consists of mineral glass.

13. The radiation apparatus according to claim 1 or 2, wherein said frame has cooling ribs (15) on its circumference.

14. The radiation apparatus according to claim 13, wherein some cooling ribs (15) are formed as thickened webs (16) and comprise throughholes (17) aligned with respect to said first and second frame halves (3, 4) for receiving fastening means.

* * * * *